(12) United States Patent
Jacobsen et al.

(10) Patent No.: US 6,766,720 B1
(45) Date of Patent: Jul. 27, 2004

(54) METHOD AND APPARATUS FOR FORMING CUTS IN CATHETERS, GUIDEWIRES AND THE LIKE

(75) Inventors: Stephen C. Jacobsen, Salt Lake City, UT (US); Clark C. Davis, Salt Lake City, UT (US)

(73) Assignee: Sarcos LC, Salt Lake City, UT (US)

( * ) Notice: Subject to any disclaimer, the term of this patent is extended or adjusted under 35 U.S.C. 154(b) by 0 days.

(21) Appl. No.: 09/470,606

(22) Filed: Dec. 22, 1999

Related U.S. Application Data (63) Continuation-in-part of application No. 08/714,555, filed on Sep. 16, 1996, now Pat. No. 6,014,919.

(51) Int. Cl.[7] .............................. B26D 5/02; B26D 5/20; B26D 7/02; B26D 7/06; B26D 7/26
(52) U.S. Cl. .............................. 83/75; 83/210; 83/211; 83/282; 83/361; 83/367; 83/368; 83/370; 83/421; 83/422; 83/466.1; 83/486; 83/886
(58) Field of Search .......................... 83/75, 62, 62.1, 83/63, 211, 361, 367, 368, 370, 209, 210, 240, 248, 257, 282, 409, 418, 421, 457, 465, 466.1, 471.2, 471.3, 485, 486, 486.1, 556, 563, 733, 863, 864, 881, 886, 750, 822; 269/254 R; 279/46.1

(56) References Cited

U.S. PATENT DOCUMENTS

| | | | |
|---|---|---|---|
| 1,553,227 A | 9/1925 | Feyk et al. ................... 83/409 |
| 1,866,888 A | 7/1932 | Hawley ...................... 83/471.3 |
| 3,686,990 A | 8/1972 | Margolien .................... 83/409 |
| 4,000,672 A | 1/1977 | Sitterer et al. ................ 83/203 |
| 4,476,754 A | 10/1984 | Ducret ........................ 83/150 |
| 4,545,390 A | 10/1985 | Leary ........................... 600/462 |
| 4,574,670 A | 3/1986 | Johnson ....................... 83/409 |
| 4,781,092 A | 11/1988 | Gaiser .......................... 83/153 |
| 4,786,220 A | 11/1988 | Fildes et al. ................. 409/134 |
| 4,884,579 A | 12/1989 | Engelson .................... 600/585 |
| 4,922,777 A | 5/1990 | Kawabata ..................... 83/452 |
| 4,954,022 A | 9/1990 | Underwood et al. ......... 408/1 R |
| 4,955,862 A | 9/1990 | Sepetka .................. 604/164.13 |
| 4,989,608 A | 2/1991 | Ratner ......................... 600/420 |
| 4,994,069 A | 2/1991 | Ritchart et al. .............. 606/191 |
| 5,009,137 A | 4/1991 | Dannatt ........................ 83/209 |
| 5,095,925 A | 3/1992 | Elledge et al. ................ 134/61 |
| 5,306,252 A | 4/1994 | Yutori et al. ................. 600/585 |
| 5,308,435 A | 5/1994 | Ruggles et al. .............. 156/465 |
| 5,315,906 A | 5/1994 | Ferenczi et al. ............... 83/27 |
| 5,376,084 A | 12/1994 | Bacich et al. ................ 604/515 |
| 5,437,288 A | 8/1995 | Swartz et al. ................ 600/585 |
| 5,438,993 A | 8/1995 | Lynch et al. ................. 600/434 |
| 5,439,000 A | 8/1995 | Gunderson et al. .......... 600/473 |
| 5,441,483 A | 8/1995 | Avitall ...................... 604/95.05 |
| 5,441,489 A | 8/1995 | Utsumi et al. ............... 604/525 |
| 5,460,187 A | 10/1995 | Daigle et al. ................ 606/194 |
| 5,477,856 A | 12/1995 | Lundquist .................... 600/373 |
| 5,520,645 A | 5/1996 | Imran et al. ................. 600/585 |
| 5,964,135 A | 10/1999 | Aihara ......................... 83/168 |
| 6,357,330 B1 * | 3/2002 | Dass et al. .................... 83/863 |

FOREIGN PATENT DOCUMENTS

| | | |
|---|---|---|
| DE | 2539191 | 9/1975 |
| EP | 0 123 456 A2 | 3/1984 |
| EP | 0 123 456 B1 | 3/1984 |
| EP | 06312313 | 8/1994 |
| GB | 1 507 057 | 9/1975 |
| GB | 2 257 269 A | 3/1989 |
| WO | PCT/US92/07619 | 9/1992 |

* cited by examiner

Primary Examiner—Charles Goodman
(74) Attorney, Agent, or Firm—Thorpe North & Western

(57) ABSTRACT

A system configured for forming precision cuts in an elongate object comprising a base member and a movable member carried by the base member and movable toward and away from the elongate member, and a cutting blade carried by the movable member; and a clamping device coupled to the base member, and configured to engage the elongate object while the cutting blade makes an incision therein; and a contact detection system configured for detecting contact between the cutting blade and the elongate object.

32 Claims, 9 Drawing Sheets

METHOD AND APPARATUS FOR FORMING CUTS IN CATHETERS, GUIDEWIRES AND THE LIKE

This application is a continuation-in-part of U.S. patent application Ser. No. 08/714,555, filed on Sep. 16, 1996 now U.S. Pat. No. 6,014,919.

BACKGROUND

1. Field of the Invention

The present invention pertains to making precision cuts in catheters and guidewires. Specifically, a device for holding, advancing, rotating and then cutting a catheter or guidewire is provided which is able to manipulate the catheter or guidewire in two degrees of freedom to enable precision control of the location of the cuts. Various clamping mechanisms are provided for manipulating the catheter or guidewire, as well as mechanisms for wear detection of saw blades and depth of cuts are used to make the cuts resulting in controlled variation in mechanical properties.

2. State of the Art

Making cuts in catheters and guidewires requires precision in order to ensure reliability because of the medical applications in which they are used. However, it is also important to control costs of production so that costs to the health care industry can be minimized.

The state of the art is typified by such devices as grinding wires, wound coils, and lasers for making the cuts. Electro Discharge Machining (EDM) is also used. Unfortunately, these devices often suffer from high cost or imprecise or difficult control mechanisms for properly positioning both the device to make the cut and the cylindrical object to be cut. With these devices it is also difficult to control the depth of cut, especially as wear increases on the cutting apparatus.

What is needed is a method and apparatus for making cuts in catheters and guidewires which allows precise control of characteristics of the cuts. This entails precision holding, advancement and rotation of the generally cylindrical object while at least one saw blade is itself advanced to make the cut and retracted afterward. A system is also needed which allows for highly precise detection of the point of contact of the blade and the cylindrical object, thus allowing precise control of the depth of cut and detection and correction for slight shape defects in the cylindrical object and wear of the blade.

OBJECTS AND SUMMARY OF THE INVENTION

It is an object of the present invention to provide a method and apparatus for forming precision cuts in catheters and guidewires.

It is another object to provide a method and apparatus for forming precision cuts in cylindrical objects.

It is yet another object to provide a method and apparatus for forming precision cuts by manipulating a cylindrical object in two degrees of freedom to control the parameters of the cuts.

It is still another object to provide a method and apparatus for holding, advancing and rotating a cylindrical object to be cut.

Still another object of the invention is to provide a method and apparatus for increasing throughput of a device which forms cuts in cylindrical objects by providing multiple saw blades on a single cutting tool.

It is another object to provide a method and apparatus for detecting the extent of wear of a saw blade in order to more precisely control the position of the saw blade.

It is still another object to provide a system which precisely detects the point of contact between the cutting blade and the cylindrical object, so as to correct for blade wear and for shape defects in the cylindrical object.

It is yet another object to provide a system for precisely measuring and controlling the depth of cut.

These and other objects of the present invention are realized in a preferred embodiment of a device for making cuts in a catheter, guidewire or other cylindrical object. The device includes a base which has at least one circular saw blade mounted on a spindle member, and a clamp for manipulating and positioning the object to be cut. The circular saw blade is rotatably mounted on the spindle member. The spindle member is free to move vertically and horizontally with respect to the base to thereby control the location, length, depth and angle of the cuts in a cylindrical object disposed adjacent thereto. The clamp is able to hold the object to be cut, as well as position it by, for example, rotation to thereby expose the entire circumference of the cylindrical object to the saw blade. By releasing the clamp, a pinch roller advances the cylindrical object before the clamp is re-engaged to securely hold the cylindrical object for cutting.

Another aspect of the invention is the ability to make precision cuts by providing means for controlling the rotation and advancement of the object to be cut and movement of the saw blade spindle member. Sensors are also provided to enable detection of wear on the saw blade so as to signal needed replacement or adjustment of the location of the saw blade spindle member to compensate.

Another aspect is the ability to simultaneously make a plurality of cuts in the object. This is accomplished with a saw blade having a plurality of blades in parallel. Even more cuts can be made by providing more than one saw blade spindle member, where each is independently movable in two degrees of freedom.

Another aspect of the invention is to provide more than one spindle member so that blades can simultaneously make precision cuts at different locations along the length of the cylindrical object.

Another aspect of the invention is to provide a system for electrical detection of contact and/or proximity between the cutting blade and the cylindrical object. The cylindrical object is grounded, while an electrical potential, either AC or DC, is applied to the blade and detected by a controller. When the blade contacts the cylindrical object, the electrical current detected by the controller jumps because of the ground connection, allowing the controller to very accurately detect the point in the blade's travel where contact occurred.

Another aspect of the invention is to provide a system wherein the electrical proximity/contact detection system is employed at a plurality of points around the circumference of the cylindrical object, so as to detect flaws in the shape of the cylindrical object, and to correct the depth of cut accordingly in order to produce a catheter/guidewire with the desired characteristics.

These and other objects, features, advantages and alternative aspects of the present invention will become apparent to those skilled in the art from a consideration of the following detailed description taken in combination with the accompanying drawings.

DETAILED DESCRIPTION OF THE INVENTION

Reference will now be made to the drawings in which the various elements of the present invention will be given numerical designations and in which the invention will be discussed so as to enable one skilled in the art to make and use the invention.

Figure 1A:
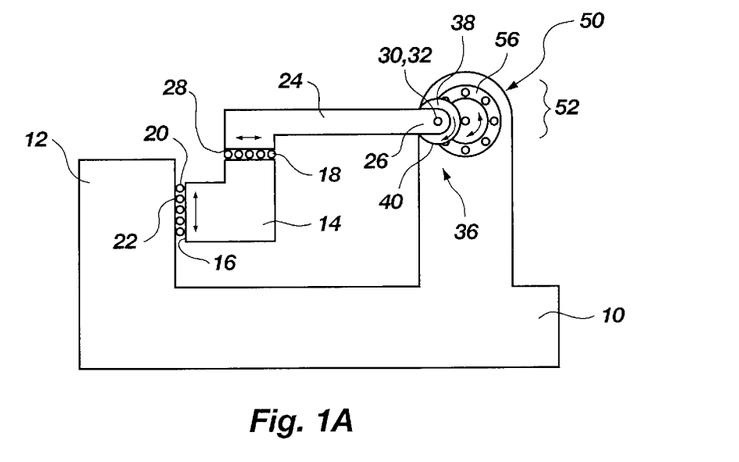
FIG. 1A is a front elevational view of a preferred embodiment made in accordance with the principles of the present invention.
Figure 1B:
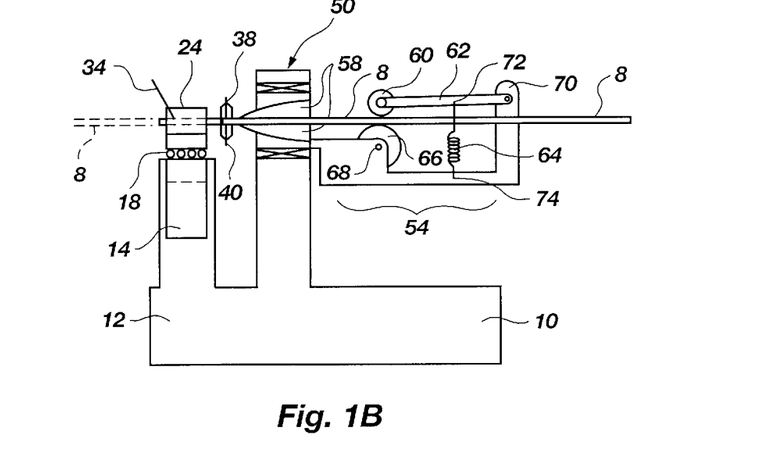
FIG. 1B is a side elevational view of the invention shown in FIG. 1A.

The present invention is illustrated in FIGS. 1A and 1B. FIG. 1A is a front view of the preferred embodiment of the invention, and shows the system for forming precision cuts in a catheter, a guidewire, or other cylindrical objects. For purposes of keeping in mind the intended use of the present invention, a catheter will be referred to as the object being cut, although any cylindrical object can be substituted for the catheter. However, reference to the catheter is only for the convenience of writing in terms of a specific cylindrical object, and should not be considered a material limitation of the invention. However, referring to a catheter keeps present in mind the objective of having a very precise cutting device, where precision is paramount in most medical applications. Furthermore, a catheter is only one embodiment of a medical application, but which easily represents the need for precision.

The system 6 shown in FIGS. 1A and 1B is comprised of several elements including a base member 10 for supporting the structure. Coupled in sliding engagement with a vertical base member 12 is a vertically movable member 14 which has a first vertical coupling face 16 and a first horizontal coupling face 18. The vertical coupling face 16 is slidingly engaged with a base member vertical coupling face 20.

The mechanism 22 for enabling the sliding engagement between the vertical coupling face 16 and the base member vertical coupling face 20 can be any appropriate apparatus. The important consideration is that the vertically movable member 14 not be permitted to move horizontally, or the precision of the system will be compromised. Therefore, the tolerances of the mechanism 22 must necessarily be small. A good example of an appropriate mechanism 22 is well known to those skilled in the art as a crossed roller bearing slide.

Figure 2:
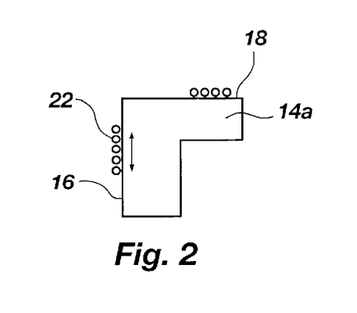
FIG. 2 is an alternative embodiment of a vertically moving member shown reversed in orientation with respect to FIGS. 1A and 1B.
Figure 3:
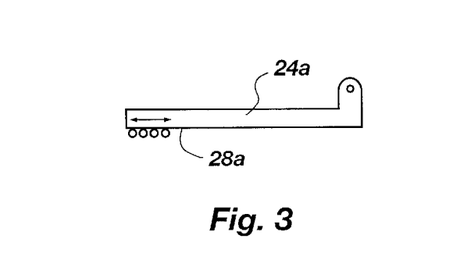
FIG. 3 is an alternative embodiment of a horizontally moving member shown reversed in orientation with respect to FIGS. 1A and 1B.

The shape of the vertically movable member 14 is shown here as a small backwards "L". An alternative shape for a vertically movable member 14a is shown in FIG. 2. The member 14a is flipped over as compared to the embodiment of FIG. 1A. The important feature of the member 14a is that it provide two faces 16, 18 which can be slidably engaged to move vertically and provide a second face on which another member can slidably engage to move horizontally. Similarly, another embodiment of a horizontally moveable member 24a is illustrated in FIG. 3. Here, a horizontal coupling face 28a is substantially planar with the horizontally moveable member 24a.

The system in FIGS. 1A and 1B is also comprised of a horizontally movable member 24 which has a spindle end 26 and a second horizontal coupling face 28. This horizontally movable member 24 is slidably engaged at its second horizontal coupling face 28 to the vertically movable member 14 at its first horizontal coupling face 18. It should be observed that the vertically movable member 14 and the horizontally movable member 24 are capable of moving independently of each other. In this way, the system achieves two independent degrees of freedom of movement.

The spindle end 26 of the horizontally movable member 24 provides a horizontal slot 30 in which a spindle 32 is disposed. The slot 30 is generally circular to serve as a receptor for the round shaft 34 of the spindle 32. The spindle shaft 34 has disposed on a working end 36 thereof at least one circular saw blade 38. The circular saw blade 38 is disposed vertically on the spindle shaft 34, but may also be angled in other embodiments.

The spindle shaft 34 is coupled to a drive motor by gears, belts, direct drive, or any other appropriate means (not shown) which will cause the spindle shaft 34 to rapidly rotate. The drive motor (not shown) can be disposed in any appropriate location relative to the spindle shaft. In a preferred embodiment, the spindle shaft 34 is driven by a brushless DC motor through a toothed timing belt.

The circular saw blade 38 is typical of those found in the art. In a preferred embodiment, the cutting edge 40 of the saw blade 38 is coated with industrial diamonds.

The means for holding and otherwise manipulating a catheter 8 to be cut is the clamping member 50. The clamping member 50 is comprised of two major assemblies: the clamp 52 and the clamp feeding (supplying) means 54, or the device which feeds the catheter 8 to and then through the clamp 52. The clamping member 50 is also coupled to the base member 10 and disposed to hold the clamp 52 in a position for easy feeding of the catheter 8 to the circular saw blade 38.

In the preferred embodiment, the clamp 52 is of the type known to those skilled in the art as a collet clamp. A collet clamp is a slotted cylindrical clamp inserted tightly into the tapered interior of a sleeve or chuck on a lathe to hold a cylindrical piece of work. In FIG. 1A, the cylindrical shape of the clamp 52 is visible. It is slotted in that the clamping arms 58 are separate from each other so that they can pull away from the catheter 8 when disengaging, and then securely come together around the catheter 8 when engaging.

In a preferred embodiment, a desirable feature of the clamp 52 is that it is rotatably mounted within the clamping member 50. The collet clamp 52 can then rotate so as to dispose a different portion of the surface of the catheter 8 to the saw blades 38. The mechanism for rotating the clamp 52 is shown generally at 56, and is comprised of the clamp 52 which is held in a frame which can rotate with respect to the saw blade 38.

The clamp feeding (supplying) means 54 seen in FIG. 1B is shown in this preferred embodiment to be comprised of a pinch roller assembly 60, 62 working in conjunction with a feed roller 66. As FIG. 1B should make clear, the pinch roller assembly 60, 62 feeds the catheter 8 to the clamp 52 by using friction created between two opposing members 60, 66. The upper member is the pinch roller 60. The lower member is the feed roller 66. The feed roller 66 has an axle 68 mounted in the clamp feeding means 54 so that the feed roller 66 can roll. The pinch roller 60 is disposed at the end of a lever arm 62 which pivots at a pivoting end 70. Located distally from the pinch roller assembly along the length of the lever arm is a hole 72. One end of a spring 64 is inserted therethrough, and the other end of the spring 64 is coupled at another hole 74 to the clamp feeding means 54. The spring 64 provides the tension necessary for the feed roller 64 to push the catheter 8 to the clamp 52.

Having described most of the components in a preferred embodiment of the catheter cutting assembly 6, the operation of the assembly 6 is as follows. First, the uncut catheter 8 is placed between the pinch roller 60 and the feed roller 66. This can be done by raising the lever arm 62 by stretching the spring 64. Releasing the lever arm 62 causes the pinch roller 60 to push down against the feed roller 66, with the catheter 8 disposed therebetween. A drive mechanism (not shown) is coupled to the feed roller 66 to cause it to roll and thereby push the catheter 8 toward the clamp 52. The clamp 52 should be in a disengaged position (hole through clamp is larger than diameter of the catheter 8) so that the catheter 8 can be fed easily therethrough. After passing through the clamp 52, the catheter 8 is fed sufficiently far past the circular saw blade 38 so that it is in a proper position to have an incision made in or through its surface.

When the catheter 8 is positioned correctly, the clamp 52 is engaged and the saw blade 38 is advanced to make cutting contact. Before cutting, the saw blade 38 will always be positioned in a retracted position. The retracted position is both vertically below and horizontally pulled away from the catheter 8. The first movement of the saw blade 38 is 1) horizontal advancement toward the catheter 8. This is accomplished by moving the horizontally movable member 24 relative to the vertically movable member 14 to which it is attached. The horizontally movable member 24 is moved until it has reach the depth of the incision to be made in the catheter 8. The next step 2) comprises the vertically movable member 14 moving upwards relative to the base 10 to which is coupled to thereby make the cut. The saw blade 38 is then immediately retracted by moving the vertically movable member 14 away from the catheter 8. The horizontal member is moved only when the next cut is at a different depth or when all cutting is complete.

If another cut is to be made, the collet clamp 52 is released as step 4). The catheter 8 is then fed through the clamp 52 by the feed roller 66 as step 5). The collet clamp 52 is then re-engaged in step 6) and, if necessary, the collet clamp 52 is rotated to expose a different position of the catheter 8 to the saw blade 38. The saw blade 38 is then moved horizontally if the depth of cut is to change, and then vertically to make the cut and steps 1) through 7) repeat as often as necessary until all the incisions have been made or the catheter 8 is no longer capable of being grasped by the feed roller 66 and opposing pinch roller 60.

The above description of the operation of the catheter cutting system 6 describes the different roles served by the clamp 52. When the circular saw blade 38 is making a cut in the catheter 8, the clamp 52 holds the catheter 8 steady. When the cut has been made in the catheter 8, the catheter 8 is fed through the clamp 52 by causing the clamp to disengage from around the catheter 8. After being disengaged, the catheter 8 is fed through the clamp 52 until the next incision point on the catheter 8 is in position relative to the saw blade 38. The clamp 52 re-engages so as to be disposed snugly around the catheter 8 to again prevent movement of the catheter 8 during cutting.

It should be recognized from the description above that the width of a cut into the catheter 8 is limited to the width of the circular saw blade 38. A wider cut therefore requires that the catheter 8 be advanced slightly past the saw blade 38. However, advancement does not take place while making a cut. The saw blade 38 must be withdrawn so that the clamp 52 can disengage from around the catheter 8 while it is advanced. This is necessary because allowing cutting of the catheter 8 when the clamp is disengaged would create a useless if not imprecise cut.

Another vital component of the assembly 6 is a position sensing means. While it is now understood how the catheter 8 is cut, it is not been explained how the feed roller 66 knows when to stop feeding the catheter 8 through the clamp 52, or how far the clamp 52 needs to rotate before cutting commences. In other words, precision cutting also requires precision positioning of the catheter. Precise positioning requires sensors which can detect where the catheter 8 is in relation to the saw blade 38 and the clamp and then provide this information to some control device which coordinates movement of all components by sending the necessary signals to correctly position all of the system 6 components.

Figure 4:
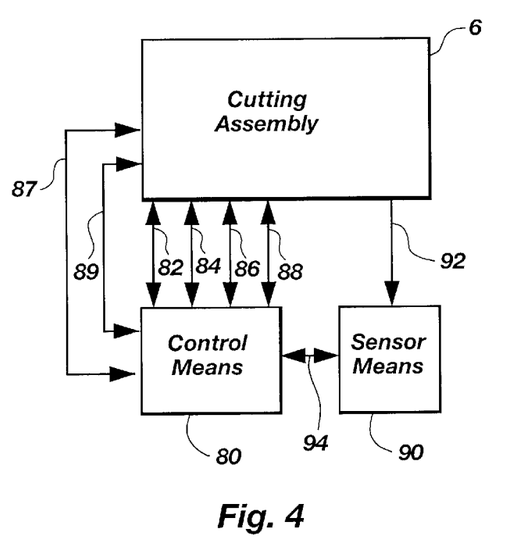
FIG. 4 is a block diagram of the preferred embodiment which shows a control means and sensor means for controlling position determination and movement of components.

This concept is shown generally in the block diagram of FIG. 4. The catheter cutting system 6 is shown as having inputs from a control means 80 for positioning the vertically movable member 14 and shown as arrow 82, the input shown as arrow 84 for positioning the horizontally movable means 24, the arrow 86 which designates an input for controlling rotation of the clamp 52, and an arrow 88 which designates an input for controlling the feed roller 66. Two control inputs for the clamp and the spindle motor are also shown as arrows 87 and 89, respectively. The block diagram in FIG. 4 also shows a sensor means 90 for receiving position information from the system 6 as indicated by arrow 92. This information is transmitted to the control means 80 as indicated by arrow 94 so that it can be processed and the correct control signals 82, 84, 86, and 88 can be transmitted to the system 6.

Figure 5:
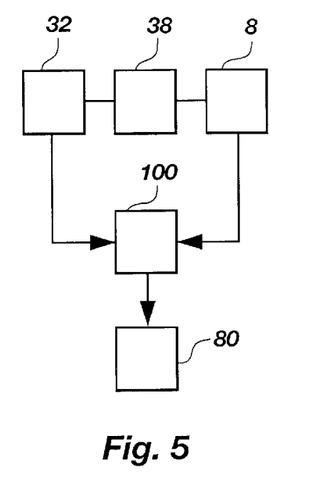
FIG. 5 is a block diagram showing signals which pass between components when using an electrical conduction sensor.

There are several alternative methods for determining the position of the catheter 8 relative to the saw blade 38. These devices can all be substituted as the sensor means 90 of FIG. 4. The first device is an electrical conduction sensing circuit 100 shown in block diagram form as FIG. 5. It is sometimes the case that the materials used in catheters 8 are electrically conductive. Furthermore, the saw blade 38 can also be electrically conductive. Consequently, bringing the saw blade 38 into contact with the conductive catheter 8 can result in the completion of an electrical circuit. By moving the saw blade 38 sufficiently slowly so as not to abruptly make contact with the catheter 8, the moment of contact can be used as a reference point so that the saw blade 38 can be moved the proper horizontal distance to make the desired cut.

Figures 6, 7:
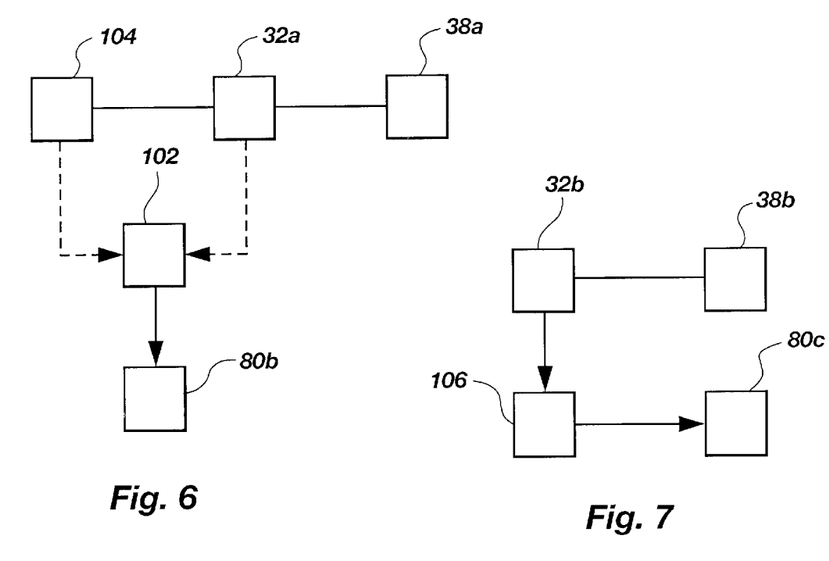
FIG. 6 is a block diagram showing signals which pass between components when using a mechanical drag detection sensor.
FIG. 7 is a block diagram showing signals which pass between components when using a rotation detector sensor.

FIG. 6 shows an alternative method of position sensing. In this embodiment, mechanical drag detection means is coupled to a saw blade 38a. The drag detection means 102 can be coupled to either the driving means 104 of the saw blade 38a, or a spindle 32a of the saw blade 38a. In other words, the drag detection means 102 is any suitable device for detecting when a dragging force is encountered by the saw blade 38a. For example, one device for this purpose is a torque transducer which measures the torque loading of the shaft which turns the blade 38a.

FIG. 7 shows a related method of position sensing is to use a rotation detector means 106 which detects even slight partial revolutions of a saw blade 38b as the spindle is oscillated vertically and slowly advanced horizontally. With the blade 38b not spinning, rotation of the blade 38b will occur when slight contact is made between the blade with the catheter.

Figure 8:
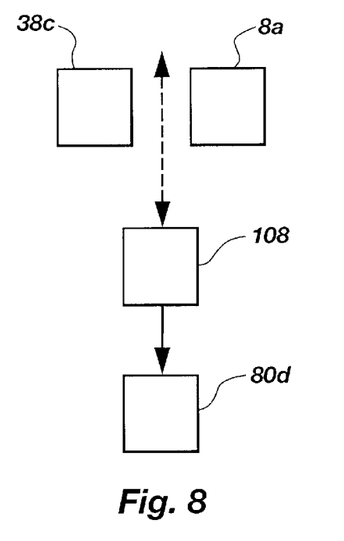
FIG. 8 is a block diagram showing signals which pass between components when using an optical detection sensor.

A final embodiment for detecting the position of a saw blade 38c relative to catheter 8a is to use an optical detector 108, as shown in block diagram form in FIG. 8. The optical detector means 108 is disposed such that it can detect contact between the saw blade 38c and the catheter 8a. There are various optical devices which can be used to implement this detector 108.

One aspect of the invention which is related to the various sensing means 90 described above is that not only is it important to know the position of the blade, but it is also important to know the degree of wear of the blade. All of the sensor embodiments above are inherently able to compensate for the wear which the blade 38 will experience. In other words, none of the methods for determining the exact position of the blade 38 rely on an assumption that the size of the blade 38 is constant. All of the sensor embodiments 90 account for saw blade 38 wear by dynamic determination of position which is not based on a predefined size of the saw blade 38. Instead, the sensors 90 determine when contact is being made, and adjust the position of the blade 38 or the catheter 8 accordingly.

Figure 9A:
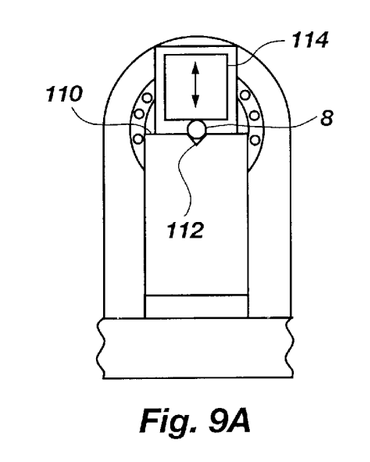
FIG. 9A is a front elevational view of an alternative embodiment for the clamping means.
Figure 9B:
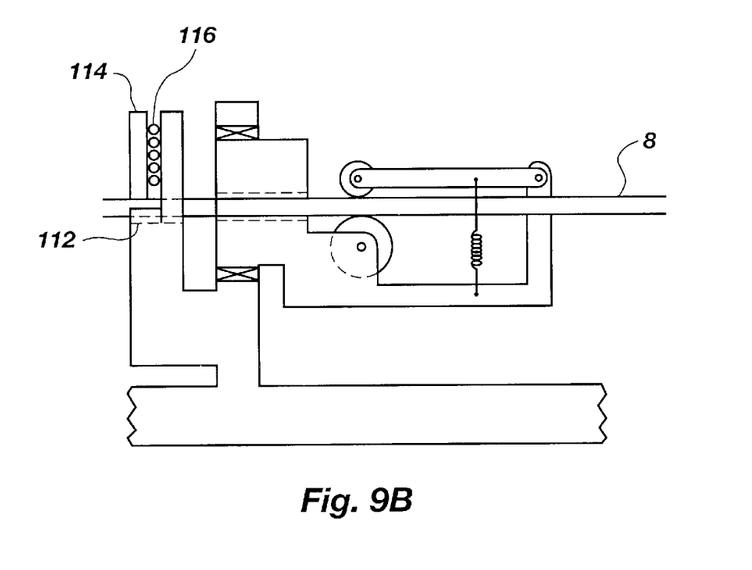
FIG. 9B is a side elevational view of the alternative embodiment for the clamping means of FIG. 9A.

Variations of the preferred embodiment are illustrated in FIGS. 9A and 9B which show that the clamping means 52 has been modified. As can be seen in FIG. 9A, a stationary support surface 110 is provided with a slot 112 therein for supporting the catheter 8 from below. The slot 112 guides and holds the catheter 8 before, during and after cutting. Holding the catheter 8 not only allows more precise cutting, but prevents damage to the catheter 8 which might otherwise occur. A movable clamping member 114 or anvil is also provided to thereby apply force to the catheter 8 which is clamped between the anvil 114 and the slotted support surface 110. FIG. 9B also shows that the anvil 114 has a mechanism 116 which allows the anvil 114 to move vertically with respect to the support surface 110.

Figure 9C:
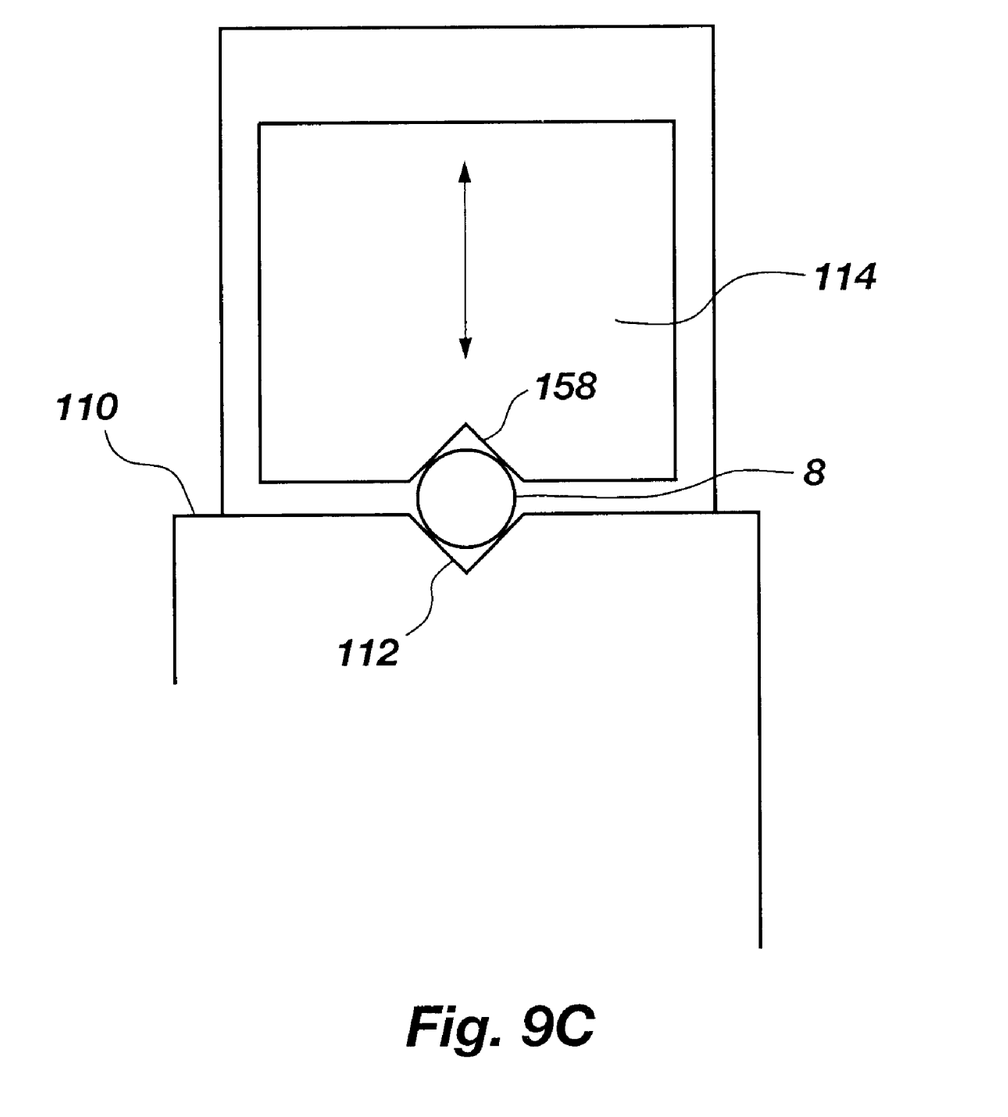
FIG. 9C is a front view which shows that the anvil has a slot.

FIG. 9C is provided to illustrate an alternative embodiment of the anvil 114. As shown, the anvil 114 has a slot 158 which will hold the catheter 8 more securely for cutting.

Figure 10:
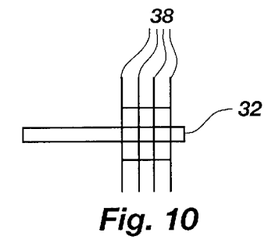
FIG. 10 is an alternative saw blade assembly which can be used in all embodiments of the present invention.

FIG. 10 illustrates a modification to the spindle 32 and saw blade 38 arrangement shown in FIGS. 1A and 1B. Specifically, a plurality of saw blades 38 are shown as being mounted in parallel on the same spindle 32. This also means that the saw blades 38 are necessarily coaxial. It is also preferred that the saw blades 38 have the same diameter so that no individual saw blade 38 makes a deeper incision in the catheter 8 than any of the others. However, it should be apparent that if the spindle 32 or the saw blades 38 are easily detachable from the system 6, then saw blades of varying diameters might be mounted on the same spindle 32 to achieve a consistent pattern of cuts having different depths.

Figure 11A:
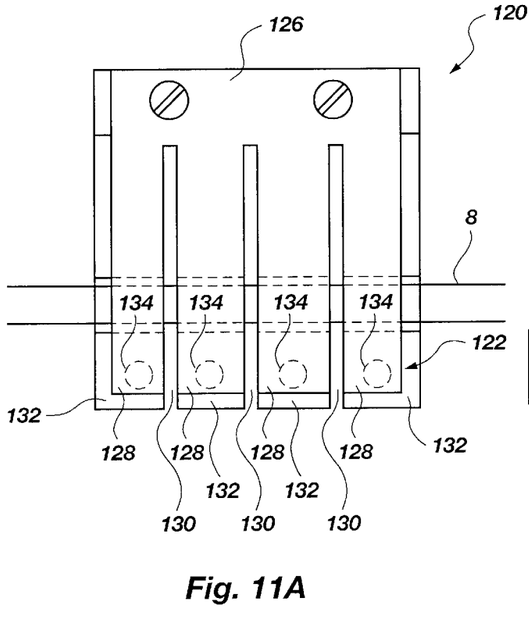
FIG. 11A is a top elevational view of an alternative clamping device.

FIG. 11A shows a clamp mechanism 120 which should be used in conjunction with the multiple saw blade 38 assembly of FIG. 10. The clamp mechanism 120 is capable of holding a catheter 8 in place while the catheter 8 is cut by the plurality of saw blades 38. This is accomplished by providing a clamping surface 122 having a depression or slot 124 for receiving the catheter 8. Coupled to the clamping surface is a leaf spring 126. The leaf spring 126 is comprised of several fingers 128 which force the catheter 8 to remain in the slot 124 while it is cut. Disposed perpendicular to the slot 124 and extending from the clamping surface 122 completely through the clamping mechanism 120 to a back side 136 are a plurality of slots 130 (which make clamp fingers 132) through which the saw blades 38 are extended to thereby cut the catheter 8. The fingers 128 of the leaf spring 126 are typically spaced apart a distance which is equal to the spacing between the plurality of slots 130. This ensures that the saw blades 38 do not inadvertently make contact with the leaf spring fingers 128 while cutting the catheter 8.

Figure 11B:
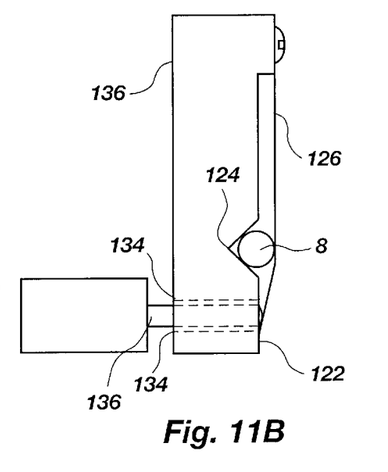
FIG. 11B is a side elevational view of the alternative clamping device of FIG. 11B.

To allow the catheter 8 to be fed through the slot 124 in the clamping surface 122, there must be a mechanism for raising the fingers 128 of the leaf spring 126 from off the clamping surface 122. FIG. 11A shows a plurality of holes 134 through the clamping mechanism 120, one hole 134 per clamp finger 132. FIG. 11B shows these holes 134, and more importantly, the plurality of push rods 136 which extend through the holes 134 from the back side 136 of the clamp mechanism 120 to the clamping surface 122. What is not shown is a lever arm or other mechanism which simultaneously pushes the plurality of push rods 136 when the clap mechanism 120 is instructed to disengage the clamp and move the catheter 8.

Figure 12:
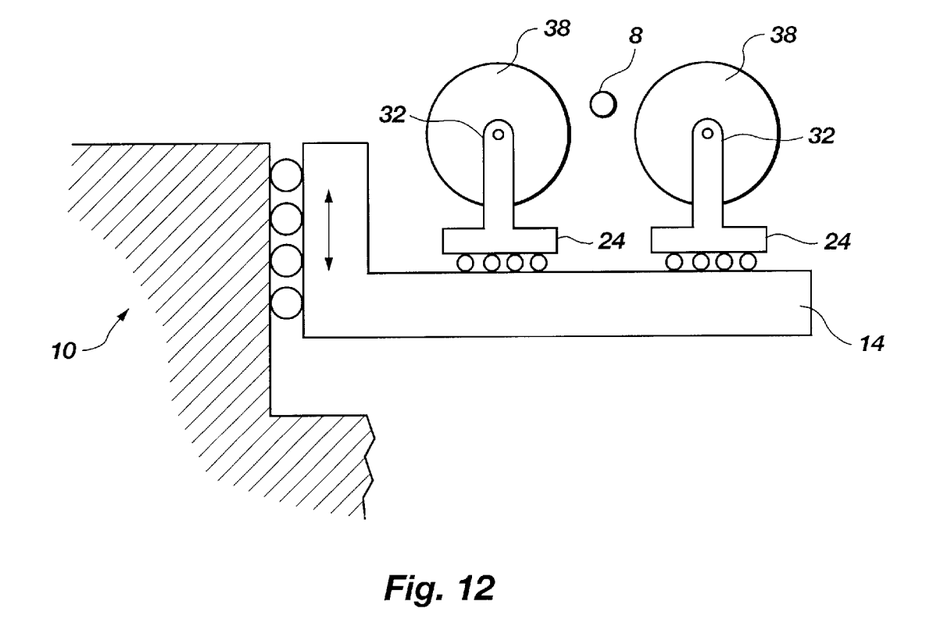
FIG. 12 is an alternative embodiment which uses two saw blade assemblies to simultaneously make incisions in the catheter.

FIG. 12 is an illustration of another alternative embodiment of the present invention. The vertically movable member 14 is shown having another shape which enables it to have disposed thereon two horizontally movable members 24, each having its own associated saw blade or blades 38.

This embodiment enables the catheter 8 to be simultaneously cut at different circumferentially defined points on the catheter surface. This is especially useful in making cuts in catheters which having multiple incisions, for example, on diametrically opposed positions on the catheter 8.

Figure 13:
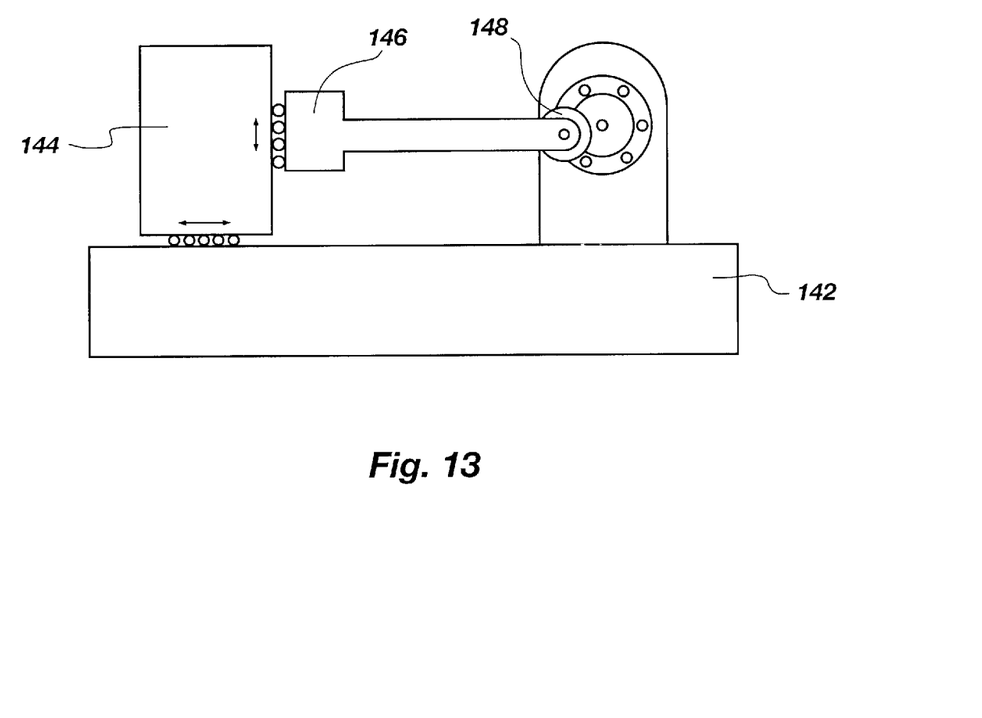
FIG. 13 is a side view of an alternative embodiment which shows a configuration with a base member, a horizontally movable member, and a vertically moveable member.

It should be noted that while the preferred embodiment has been defined as having a horizontally movable member with the spindle for the saw blade coupled thereto, the placement of the vertically and horizontally movable members can be switched as shown in FIG. 13. In this arrangement, the horizontally movable member 144 is coupled to the base member 142 and the vertically movable member 146, and the vertically movable member 146 has a spindle 148 rotatably coupled thereto.

Figure 14:
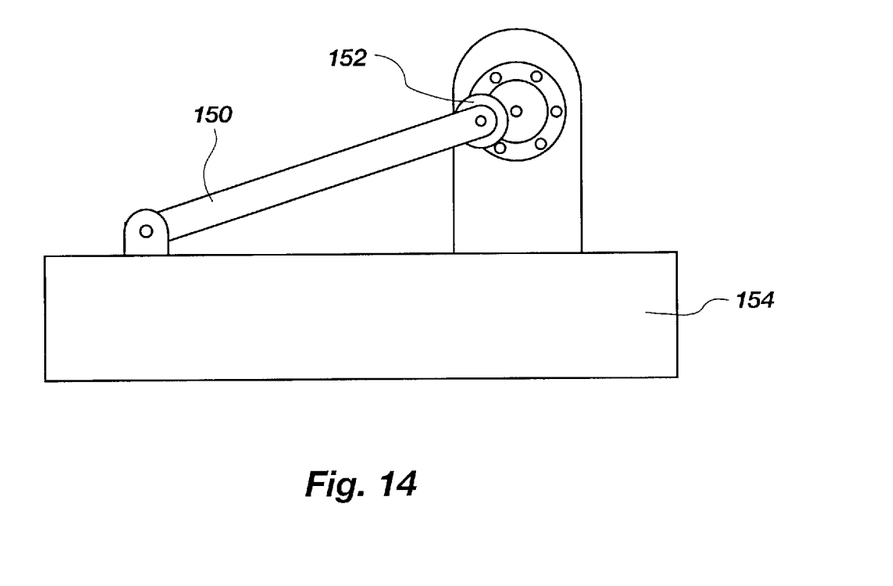
FIG. 14 is another side view of an alternative embodiment which shows a configuration of a base member, and a lever arm which moves the cutting blade in horizontal and vertical directions.

In another alternative embodiment of the present invention, shown in FIG. 14, a lever arm 150 is pivotally connected to the base member 154, and is capable of movement in at least two degrees of freedom so that it can move vertically and horizontally to position a spindle end 152.

Another aspect of the invention which should be clarified is that rotating the catheter is not limited to using a rotatable clamping mechanism. For example, the clamp can be non-rotatable and disengaged to enable the catheter feeding mechanism to rotate the catheter, and then reengage the clamp to make additional incisions. Furthermore, the clamp and the catheter feeding mechanism can be rotated together before additional incisions are made.

Alternative aspects of the invention include the substitution of a non-mechanical cutting instrument for the rotating blade of the presently preferred embodiment. For example, a laser can be provided for cutting through materials which are mounted on the system.

It should also be realized that rotating blades are not the only type of mechanical blade which can be utilized. Conventioned "sawing" blades can also be provided.

Figure 15:
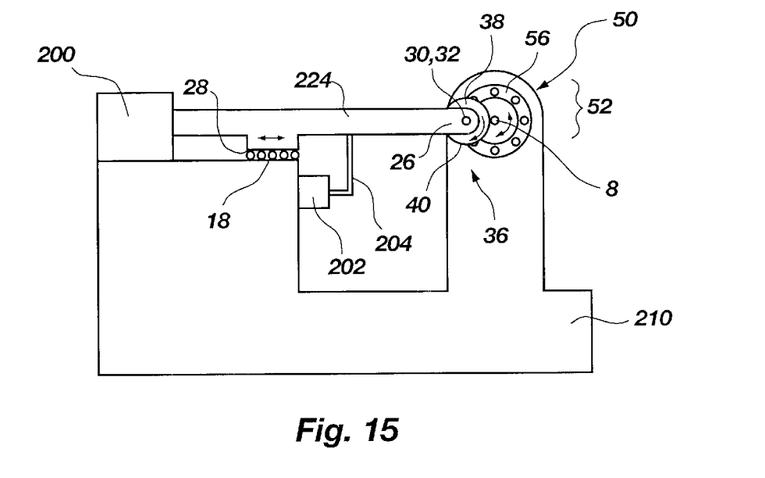
FIG. 15 is a schematic view of an alternative embodiment of the invention comprising a horizontally movable member and movement detection system.

FIG. 15 is a schematic view of an alternative embodiment of the invention. This embodiment is similar in most respects to that of FIG. 1 and includes most of same elements. For a complete description of the common elements, see the description of FIG. 1 above. However, rather than having a vertically movable member 14 as in FIG. 1, this embodiment comprises only a horizontally movable member 224 which is slidingly coupled to base member 210 at horizontal coupling face 18. In this embodiment the horizontally movable member is vertically positioned so that the center of blade 38 is in substantial alignment with the center of the catheter 8.

Horizontally movable member 224 is connected to and actuated by a linear motion transducer 200, which is affixed to base 210. Linear motion transducer 200 may comprise any device suitable for causing very accurate, controllable forward and backward horizontal motion of member 224, such as electric motors, hydraulic systems, etc. In the preferred embodiment, the linear motion transducer 200 comprises an electric stepping motor, which is coupled to member 224 via a highly accurate gear reduction system (not shown) similar to that found in a micrometer. This configuration advantageously allows motion of the horizontally movable member in very small increments.

Also affixed to base 210 is a sensor 202, which is connected via linkage 204 to horizontally movable member 224. Sensor 202 provides independent detection and measuring of the forward or backward position of horizontally movable member 224, and is connected to controller 80 as described in more detail below. Sensor 202 is preferably an optical linear encoder, but may alternatively comprise a rotary optical encoder, a linearly variable differential transformer (LVDT), a linearly variable differential capacitor (LVDC), or any other suitably accurate means of measuring the physical position of member 224. Optical encoders, LVDT's, LVDC's, and similar devices are commercially available and well known to persons skilled in the art.

Sensor 202 is optional, however. As an alternative, the extension and retraction of member 224 may simply be monitored through control of transducer 200, by monitoring the amount of extension of the stepper motor. For example, a rotary optical encoder may be interconnected to the gear reduction system that is part of transducer 200, and gauge the amount of linear extension of member 224 by monitoring the total angular rotation of the optical encoder at any given time. Rotation of the rear reduction system may be controlled by software in the controller which receives feedback from the optical encoder.

Figure 16:
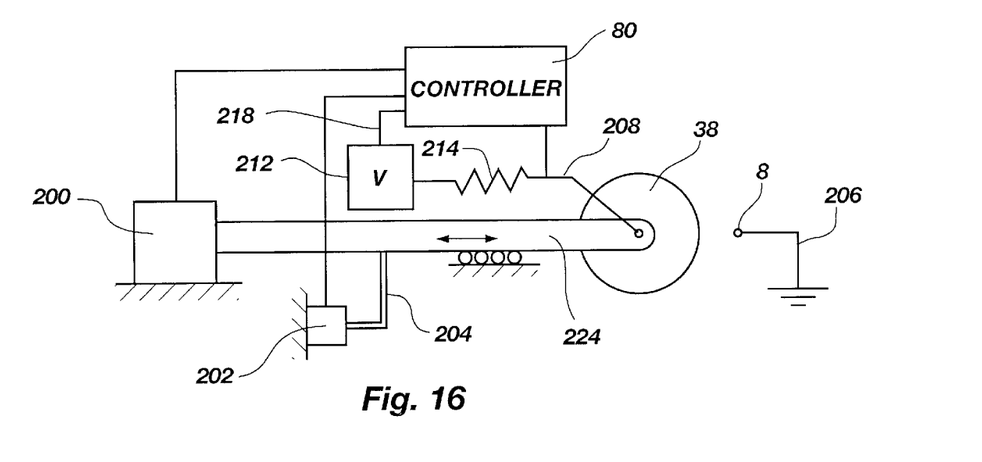
FIG. 16 is an electrical schematic view of a contact detection configuration for use with the present invention.

When making precision cuts in a catheter or guidewire, it is desirable to correct for wear of the cutting blade, and also to have a means for precisely measuring and controlling the depth of cut. FIG. 16 provides a partial schematic view of the embodiment of FIG. 15 which incorporates an electrical contact detection system to provide these desirable features. In this system, the catheter 8, which is electrically conductive, is grounded via line 206. Blade 38, which is also electrically conductive, is connected via line 208 to voltage source 212 through resistor 214, thus creating a voltage potential between blade 38 and catheter 8. It will be apparent that any cutting fluid or coolant used in conjunction with this system will need to be non-conductive.

When blade 38 is separated from catheter 8, the voltage in line 208 will be the same as the voltage produced by the voltage source 212, as reduced by resistor 214. However, when blade 38 approaches to within a few millionths of an inch of the surface of catheter 8, which is grounded, electric current will arc across the gap, causing an immediate voltage jump in line 208. The direction of this voltage jump will be dependent upon whether the system operates on direct current of alternating current. By detecting the instant that the voltage jumps and comparing this with known information regarding the position of horizontal member 224, the system can continuously verify and adjust its operation to produce highly accurate and consistent cuts.

Line 216 connects line 208 to controller 80, which is thus able to gauge the voltage in line 208, and detect when that voltage drops to zero. Controller 80 is connected back to voltage source 212 through line 218, and also connected to linear motion transducer 200 and sensor 202 for feedback and control. The controller is thus able to very accurately monitor and adjust the depth of cut by detecting the moment of contact between the blade 38 and catheter 8, sensing, through sensor 202, the exact position of member 224 when such contact is made, and adjusting the motion of member 224 through signals to transducer 200.

As an operative example, as blade 38 becomes worn through use, its diameter will decrease, causing it to contact the surface of the catheter 8 at a later and later point in its horizontal motion. If the depth of cut were determined solely by transducer settings established at the beginning of an operation, the cuts would thus become gradually shallower, thus affecting the quality and characteristics of the finished product. However, because the controller 80 sense the contact of the blade 38 with the catheter 8 at the beginning of each cut, and simultaneously receives true position information from sensor 202, the controller can signal transducer 200 to extend member 224 the appropriate distance each time to maintain the proper depth of cut.

Figure 17:
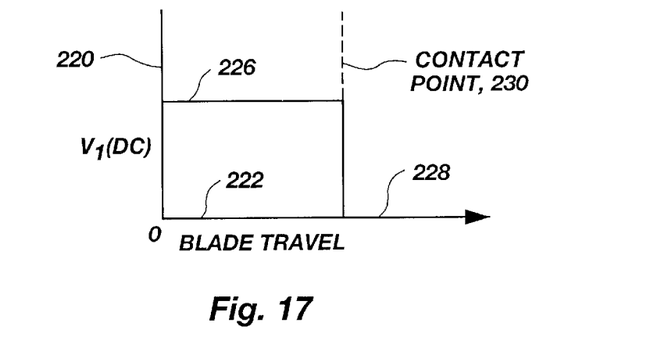
FIG. 17 is a graph of the DC voltage versus travel of the blade toward the cylindrical object for a DC contact detection circuit.

It will be apparent that the system depicted in FIG. 16 could be constructed to operate on either direct current (DC) or alternating current (AC). FIG. 17 is a graph of the line voltage $V_1$ (vertical axis 220) versus blade travel (horizontal axis 222) toward the cylindrical object, for a DC contact detection circuit. The voltage $V_1$ is constant as shown at 226 when the blade and catheter are separated, but jumps to zero as shown at 228 when the blade reaches the contact point 230, a few millionths of an inch from the surface of the catheter. In a preferred embodiment, the DC line voltage $V_1$ is 5 volts, to make the system compatible with standard digital controllers. The voltage state is thus recognizable by the controller as a digital signal representing on or off, contacting or not contacting.

Figure 18:
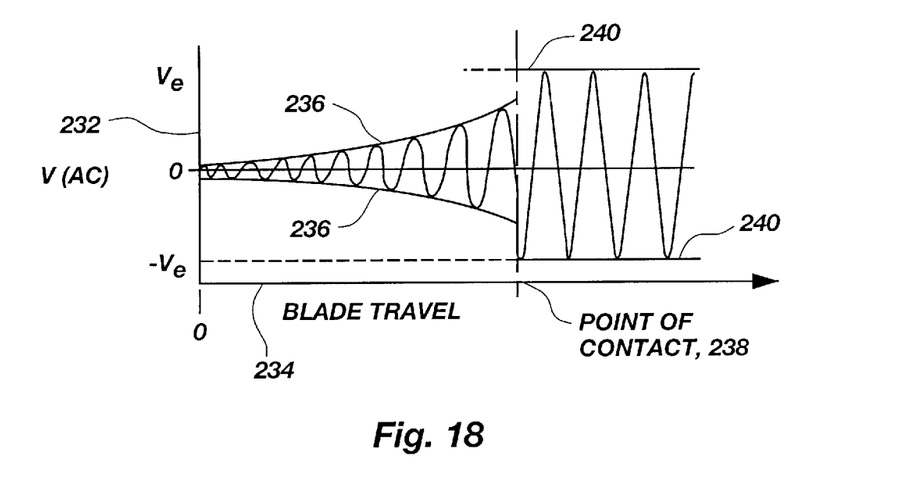
FIG. 18 is a graph of the excitation voltage versus proximity to the surface of the cylindrical object for an AC contact detection circuit.

When using AC, the system of FIG. 16 not only detects contact between the blade and the catheter, but also detects proximity using capacitative characteristics. With AC, the voltage potential between the blade and the catheter will have both a positive excitation voltage ($V_e$) and a negative excitation voltage ($-V_e$). FIG. 18 provides a graph of the excitation voltage $V_e$ (vertical axis 232) versus proximity to the surface of the cylindrical object (horizontal axis 234) for an AC contact detection circuit. As the blade approaches the surface of the catheter, the excitation voltage $V_e$ will increase in a predictable manner, from zero to some voltage between $V_e$ and $-V_e$, the variation of this voltage being represented by curves 236. Those skilled in the art will recognize that curve 236 can be predicted using principles of capacitance, and thus a controller receiving a signal representative thereof can calculate the distance between the blade and the catheter based upon the detected $V_e$.

When the blade reaches the contact point 238, a few millionths of an inch from the surface of the catheter, rather than jumping to zero, the detected voltage will immediately jump to the full value of $V_e$ as shown at 240. As with the DC embodiment, by detecting this jump in AC voltage, the controller can accurately detect the location of the edge of the catheter relative to the blade and member 224, and adjust the system as necessary.

Figure 19:
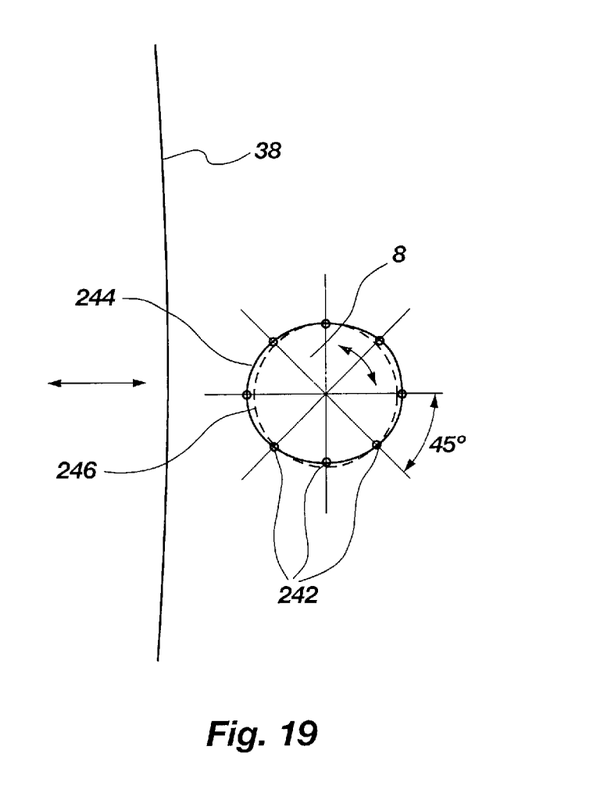
FIG. 19 shows a cross-sectional view of the system for detecting defects in the shape of the cylindrical object.

An additional advantage of this system is the ability to correct for irregularities in the material of the catheter. It will be apparent that the very fine solid or tubular wires anticipated by this invention may suffer from manufacturing flaws which are typical to wires of all kinds, such as variations in diameter, out-of-roundness, etc. Moreover, these irregularities may vary along the length of the wire. Detection and correction for these flaws is possible with the present system. FIG. 19 shows a cross-sectional view of the system for detecting defects in the shape of the cylindrical object.

When the system of FIG. 16 is in operation, the location of the surface of the catheter 8 is detected each time the blade 38 contacts it. As contact are made in the catheter at various angular locations 242, shown here as every 45 degrees, the roundness and dimension of the catheter cross-section can be detected and recorded. As shown in FIG. 19, the outer surface 244 of the catheter is irregular with respect to a theoretical round cross-section 246.

Because the system detects this irregularity, controller 80 can compensate for it by adjusting the depth of any given cut to produce a catheter with the desired properties. For example, if the catheter is detected to be 5% out of round (either large or smaller than the theoretical diameter) about a first axis, and 10% out of round (larger or smaller) about a second axis, the system may compensate by adjusting the depth of cuts relative to the first axis by 5% (either shallower or deeper), and relative to the second axis by 10% (shallower or deeper). Alternatively, the controller may be programmed to calculate the moment of inertia of the detected cross-sectional shape relative to various axes, and adjust the depth of any given cut to ensure that the resulting catheter has the desired moment of inertia at the given location, despite an irregular shape. As cutting proceeds, the irregularities may vary, but this will also be detected in an ongoing manner as described.

Additional advantages may also be realized with the present invention. For example, a series of cuts made as described may be formed on a catheter or guidewire to create an SPC symbol or bar code for identification. The inventors have found that a series of cuts can easily accommodate 100 bits of information, which may be used to indicate the batch number of a particular catheter, its material suppliers, its date of manufacture, etc. Such a bar code could be located at any location along the catheter, and could be used, for example, to allow patient specific manufacture of a catheter guidewire. If a patient required a particular sensitive catheter procedure and presented uniquely difficult vascular anatomy, but could wait for the procedure for a few days, a physician could send MRI or other diagnostic information indicating that anatomy to the manufacturer of the catheter. Then, a catheter or guidewire having the location specific flexibility particularly designed for that patient could be custom produced, and micromachined with a unique SPC code. When the physician receives that catheter, he simply scans the code to verify that he has the correct item, and then begins the medical procedure.

It is to be understood that the above-described embodiments are only illustrative of the application of the principles of the present invention. Numerous modifications and alternative arrangements may be devised by those skilled in the art without departing from the spirit and scope of the present invention. The appended claims are intended to cover such modifications and arrangements.

What is claimed is:

1. A system for forming precision cuts in an elongate object having a lengthwise axis, said system comprising:

a base;

a cutting instrument;

a moveable member movably carried by the base, configured to facilitate relative movement of the cutting instrument and the elongate object toward and away from each other so as to facilitate cutting of the elongate object by the cutting instrument;

an apparatus carried by one of the base and the moveable member and configured to hold the elongate object and translate and rotate the elongate object along, and around, respectively, the lengthwise axis of the elongate object, a linear motion transducer configured to move the elongate object and cutting instrument with respect to each other with precision;

a clamping device configured to steady the elongate object during cutting;

a contact detection system further comprising a sensor configured for detecting contact between the cutting instrument and the elongate object; and, a controller configured to cooperate with the contact detection system and to control the relative movement of the elongate object and the cutting instrument, so as to control relative movement toward and away from each other, holding and releasing of the elongate object, relative translation and rotation of the cutting instrument and the elongate object along, and around, respectively, the lengthwise axis of the elongate member, and thereby control and facilitate precision relative positioning and depth of a plurality of cuts in the elongate object.

2. A system as in claim 1, further comprising:

a rotatable spindle carried by the moveable member, wherein the cutting instrument comprises a circular cutting blade carried by the rotatable spindle; and, a drive motor coupled to the at least one spindle, and configured for rotating the cutting blade; and, wherein the apparatus configured to hold the elongate object and translate and rotate the elongate object along, and around, the lengthwise axis of the elongate object further comprises a pinch roller assembly.

3. A system as defined in claim 1, wherein the cutting instrument further comprises:

a plurality of circular saw blades mounted coaxially on the spindle; and wherein the plurality of circular saw blades are equal in diameter.

4. A system as defined in claim 1, wherein the cutting instrument comprises a cutting blade, and the controller, linear motion transducer, and contact detection system are configured to cooperate to sense wear of the cutting blade.

5. The system as defined in claim 1, wherein the cutting instrument comprises a cutting blade and the contact detection system comprises an electrical conduction sensing circuit couplable to the cutting blade to the elongate object, wherein the elongate object is conductive, and said circuit being configured for notifying the controller when the cutting blade comes into contact with the electrically conductive elongate object.

6. A system as defined in claim 1, wherein the cutting instrument comprises a cutting blade and the contact detection system comprises a mechanical drag detector operatively coupled to the cutting blade so as to sense when the blade contacts the elongate object.

7. A system as defined in claim 6, wherein the cutting blade is a circular rotatable blade and the mechanical drag detector comprises a rotation speed change detector which monitors rotation of the cutting blade and indicates a change in rotation speed, thereby determining when contact is made with the elongate object.

8. A system as defined in claim 6, wherein the mechanical drag detector comprises a torque detector which monitors a change in an amount of torque required to turn the cutting blade.

9. A system as defined in claim 1, wherein the cutting instrument is a cutting blade, and the contact detection system comprises an optical detector configured for detecting a gap between the cutting blade and the elongate object.

10. A system as defined in claim 1, wherein the clamping device is configured to grip and release the elongate object under control of the controller, the elongate object being gripped by the clamping device when the cutting instrument is cutting the elongate object, and released by the clamping device when the elongate object is moved.

11. A system as defined in claim 1, wherein the cutting instrument comprises a saw blade.

12. A system as defined in claim 1, wherein the contact detection system comprises:

an electrical conduction sensor comprising an electrical circuit operatively couplable to the cutting instrument and the elongate object, wherein the elongate object and cutting instrument are conductive, said circuit being configured to produce a signal indicating that the cutting instrument has come into contact with the electrically conductive elongate object, whereby control of a depth of cut into the elongate object from a location of said contact is facilitated.

13. A system as set forth in claim 1, wherein the apparatus configured to translate and rotate the elongate object along, and around, respectively, the lengthwise axis of the elongate object further comprises a further clamp configured to rotate with respect to the base and to simultaneously hold and rotate the elongate cylindrical object.

14. A system for forming precision cuts in an elongate object having a lengthwise axis, said system comprising:

a base;

a moveable member carried by the base;

a circular rotatable cutting blade rotatably carried by the movable member;

an apparatus, carried by the base, configured to grasp the elongate object and translate and rotate the elongate object along, and around, respectively, the lengthwise axis of the elongate object;

a clamp coupled to the base, and configured for holding the elongate object steady while the cutting blade makes an incision therein and releasing the elongate object when said apparatus manipulates the elongate object;

a contact detection system configured for detecting contact between the cutting blade and the elongate object; and, a controller, and at least one transducer, configured to cooperate with the contact detection system and to control and coordinate movement of the movable member and said cutting blade carried thereon, the clamp, and said apparatus configured to translate and rotate the elongate object, the system being configured to provide precision automatic cutting of the elongate object and precision in relative positioning of cuts, both along, and rotated with respect to, the lengthwise axis of the elongate object, and precision in depth of cuts made in the elongate object from a point of first contact between the cutting blade and the elongate object.

15. A system as defined in claim 14, further comprising means for determining an extent of wear of the cutting blade.

16. A system as defined in claim 15, wherein the contact detection system comprises a mechanical drag detector configured for detecting drag on the blade while cutting.

17. A system as defined in claim 16, wherein the mechanical drag detector comprises a rotation detector which monitors rotation of the cutting blade, thereby determining when contact is made with the elongate object.

18. A system as defined in claim 16, wherein the mechanical drag detector comprises a torque detector which monitors a change in an amount of torque required to turn the cutting blade.

19. A system as defined in claim 15, wherein the means for determining an extent of wear of the cutting blade comprises an optical detector for detecting a gap between the cutting blade and the elongate object.

20. A system as defined in claim 14, wherein the at least one transducer comprises a precise linear motion transducer cooperating with the controller to control movement of the moveable member toward and away from the elongate object.

21. A system as defined in claim 20, wherein the contact detection system further comprises:
- an electrical conduction sensing circuit coupled to the cutting blade and the elongate object, wherein the elongate object and the blade are conductive, said circuit being configured to produce a signal indicating that the cutting blade is one of: i) immediately adjacent; and, ii) in contact with, the electrically conductive elongate object.

22. A system as defined in claim 14, wherein the contact detection system comprises a mechanical drag detection means configured for detecting drag on the blade while cutting.

23. A system as defined in claim 22, wherein the mechanical drag detection means comprises a rotation detector which monitors a rate of rotation of the cutting blade, thereby determining when contact is made with the elongate object.

24. A system as defined in claim 22, wherein the mechanical drag detection means comprises a torque detector which monitors a change in an amount of torque required to turn the cutting blade while cutting.

25. A system as defined in claim 14, wherein the contact detection system comprises an optical detector for detecting a gap between the cutting blade and the elongate object.

26. A system for forming precision cuts in a small-diameter elongate cylindrical object configured to be used in one of a catheter and a guidewire configured for use in a patient's anatomy, said object having a lengthwise axis, said system comprising:
- a base;
- a horizontally moveable member carried by the base and configured to move horizontally with respect to the base;
- a linear motion transducer configured for moving the horizontally moveable member with respect to the base;
- a rotatable spindle carried by the horizontally movable member;
- a cutting blade disposed on the rotatable spindle;
- a clamping device coupled to the base member, and configured for steadying the cylindrical object while the cutting blade makes an incision therein;
- an apparatus configured to translate and rotate the elongate object along, and around, respectively, the lengthwise axis of the elongate object;
- a contact detection system comprising a contact sensor configured for detecting contact between the cutting blade and the cylindrical object and producing a signal indicative thereof; and,
- a controller configured to cooperate with the contact sensor indicating contact between the cutting blade and the cylindrical object to control relative movement of the elongate object and the cutting blade, so as to thereby control and facilitate precision relative positioning and depth of a plurality of cuts in the elongate object.

27. A system as set forth in claim 26, wherein the contact detection system further comprises:
- an electrical conduction sensing circuit coupled to the cutting blade and the cylindrical object, wherein the cylindrical object and the blade are conductive, said circuit being configured to produce the signal indicating that the cutting blade is one of: i) immediately adjacent; and, ii) in contact with, the electrically conductive cylindrical object.

28. A system as set forth in claim 27, wherein the sensing circuit employs a substantially constant direct current.

29. A system as set forth in claim 27, wherein the sensing circuit employs an oscillating current.

30. A system as set forth in claim 29, wherein the sensing circuit employs a current of alternating polarity.

31. A system as set forth in claim 27, wherein the apparatus configured to translate and rotate the elongate object along, and around, respectively, the lengthwise axis of the elongate object further comprises a further clamp configured to rotate with respect to the base and to simultaneously hold and rotate the elongate cylindrical object.

32. A system as set forth in claim 31, where the clamp comprises a non-rotating clamp immediately adjacent a location where the cutting blade contacts the elongate cylindrical object and is intermediate the further clamp and said location where the cutting blade contacts the elongate cylindrical object.

* * * * *